(12) United States Patent
Rieley et al.

(10) Patent No.: US 6,616,921 B2
(45) Date of Patent: Sep. 9, 2003

(54) ANTIPERSPIRANT PRODUCTS

(75) Inventors: Hugh Rieley, Bebington (GB); Ian Karl Smith, Bebington (GB)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 0 days.

(21) Appl. No.: 10/025,243

(22) Filed: Dec. 19, 2001

(65) Prior Publication Data

US 2002/0119108 A1 Aug. 29, 2002

(30) Foreign Application Priority Data

Dec. 21, 2000 (GB) .............................................. 0031264

(51) Int. Cl.[7] .............................. A61K 7/32; A61K 7/60; A61K 31/74
(52) U.S. Cl. .................. 424/65; 424/78.02; 424/78.08; 424/400; 424/401
(58) Field of Search ................................. 424/65, 78.02, 424/78.08, 400, 401

(56) References Cited

U.S. PATENT DOCUMENTS

| | | | |
|---|---|---|---|
| 3,966,902 A | 6/1976 | Chromecek | 424/59 |
| 4,743,440 A | 5/1988 | Callingham et al. | 424/46 |
| 5,194,262 A | 3/1993 | Goldberg et al. | 424/401 |
| 5,271,932 A | 12/1993 | Savage et al. | 424/93 |
| 6,319,491 B1 | 11/2001 | Whipple | 424/65 |

FOREIGN PATENT DOCUMENTS

| | | |
|---|---|---|
| EP | 222 580 | 5/1987 |
| EP | 260 030 | 3/1988 |
| EP | 478 327 | 4/1992 |
| EP | 0 640 335 | 3/1995 |
| EP | 701 812 | 3/1996 |
| GB | 714551 | 8/1952 |
| GB | 957175 | 5/1960 |
| JP | 2 290810 | 11/1990 |
| WO | 93/24105 | 12/1993 |
| WO | 95/27473 | 10/1995 |
| WO | 98/48768 | 11/1998 |
| WO | 98/50005 | 11/1998 |

OTHER PUBLICATIONS

GB Search Report in a GB application GB 0031264.5.
Derwent Abstract of JP 2290810, published Nov. 30, 1990.
PCT International Search Report in a PCT application PCT/EP 01/13253.

*Primary Examiner*—Shelley A. Dodson
(74) *Attorney, Agent, or Firm*—Kevin J. Stein

(57) ABSTRACT

Antiperspirant products and methods for achieving antiperspirancy utilising compositions comprising an antiperspirant salt and a water soluble polymer, characterised in that:

(i) the polymer comprises Brønsted acid groups and acts as a co-gellant for the antiperspirant salt when mixed therewith in the presence of water; and
(ii) the polymer is physically separate from antiperspirant salt prior to application.

21 Claims, No Drawings

ANTIPERSPIRANT PRODUCTS

FIELD OF INVENTION

This invention relates to the field of antiperspirant deodorant products. More specifically, it relates to antiperspirant deodorant products comprising an antiperspirant salt and a water soluble polymer that comprises Brønsted acid groups and acts as a co-gellant for the antiperspirant salt when mixed therewith in the presence of water.

BACKGROUND OF INVENTION

Cosmetic antiperspirant and deodorant products are known. Typical antiperspirant products comprise topically acceptable compositions containing a metal salt, such as an astringent aluminium or aluminium/zirconium salt, in combination with a cosmetically suitable vehicle. Typical deodorant products comprise topically acceptable compositions containing one or more agents that mask or inhibit the formation of unpleasant body odours; antimicrobial agents are widely used for this purpose. Such cosmetic antiperspirant and deodorant products may be available in a variety of product forms, for example as sticks, creams, soft-solids, roll-on lotions, aerosols, pump sprays and squeeze sprays.

Whilst such compositions provide a degree of antiperspirancy and malodour reduction, there can be problems associated with their use and there is always a desire for improved performance. A problem encountered by some people, is that the application of high levels of astringent antiperspirant salts leads to skin irritation. Others find similar problems with certain antimicrobial agents. Other problems include formulation difficulties with the high levels of active ingredients sometimes required. It has long been desirable to achieve excellent protection from body malodour without the use of high concentrations of conventional antiperspirant or deodorant agents. This could lead to antiperspirant and deodorant products being cheaper, easier to formulate (by virtue of the reduced amount of antiperspirant active used), or generally having improved sensory properties. Other benefits of requiring lesser amounts of conventional antiperspirant or deodorant agents include the reduced concentration on the body of such 'foreign' agents and the reduced impact on the environment, in terms of chemical usage and processing.

The above problems have been addressed in a number of ways in the past, examples including the use of certain polymers as antiperspirant actives. WO 93/24105 (Tranner) describes the use of particular water-insoluble film-forming polymers, with conventional antiperspirant salts being non-essential, optional components in the compositions of the invention. The examples given that include antiperspirant salt also comprise co-polymers of octylacrylamide/acrylates or PVP/acrylates. No reference is made to interactions between the antiperspirant salts and the polymers. References to film-forming polymers are also made in JP 2290810 (Nakagawa et al) and WO 95/27473 (Causton and Baines). An alternative approach is described in EP 701812 (Abrutyn et al), where porous polymer beads are claimed to be capable of absorbing sweat components.

Polymers have also been used to enhance the performance of antiperspirant salts by increasing the residual amount of antiperspirant salt on the skin. Thus, EP 222580 (Klein and Sykes) describes the use of dimethyldiallyl ammonium chloride (DMDAAC) polymers for this purpose.

The use of DMDAAC/acrylic acid-type co-polymers to thicken personal care products is described in EP 266,111 (Boothe et al) and EP 478,327 (Melby and Boothe). The latter of these patents discusses the thickening of metal-containing aqueous compositions by said co-polymers.

Aqueous compositions comprising an acrylic acid containing polymer and an antiperspirant salt are described in WO 98/50005 and WO 98/48768 (Ron et al). In these patents, the proposed invention relates to the reverse thermal viscosifying benefit of the polymer.

U.S. Pat. Nos. 5,194,262 and 5,271,932 (Goldberg et al) describe antiperspirant compositions containing microcapsules comprising an antiperspirant salt encapsulated within a water-soluble shell possessing a bioadhesive. Polyacrylic acid is disclosed as a possible component of both the water-soluble shell and the bioadhesive.

SUMMARY OF INVENTION

We have discovered that the performance of conventional antiperspirant salts can be improved by the addition of polymers that are capable of interacting with the antiperspirant salts on contact with the skin.

Thus, according to a first aspect of the present invention, there is provided an antiperspirant product comprising an antiperspirant salt and a water soluble polymer, characterised in that:

(i) the polymer comprises Brønsted acid groups and acts as a co-gellant for the antiperspirant salt when mixed therewith in the presence of water; and (ii) the polymer is physically separate from antiperspirant salt prior to application.

According to a second aspect of the present invention, there is provided a cosmetic method of achieving an antiperspirancy and/or deodorancy benefit, said method comprising the topical application to the human body of an antiperspirant product as defined in the first aspect of the invention.

According to a related aspect of the invention, there is provided a cosmetic method of achieving an antiperspirancy and/or deodorancy benefit, said method comprising bringing together on the surface of the human body an antiperspirant salt and a water soluble polymer comprising Brønsted acid groups which, in the presence of water, acts as a co-gellant for the antiperspirant salt.

According to a third aspect of the present invention, there is provided a method for the manufacture of an antiperspirant composition, comprising the mixing, in a fluid carrier material, of an antiperspirant salt and a water soluble polymer, wherein said polymer comprises Brønsted acid groups and acts as a co-gellant for the antiperspirant salt, when mixed therewith in the presence of water, and wherein the polymer is physically separate from antiperspirant salt in the composition.

DETAILED DESCRIPTION OF THE INVENTION

The interaction between the antiperspirant (AP) salt and the polymer, on application to the human body, is an essential factor in this invention. The interaction between the components is chemical in nature and results in a thickened or gelled state of matter. It is desirable that the interaction between the components does not occur significantly before they are brought into contact with the human body. Such premature interaction can result in numerous problems including unwanted thickening of the product, poor dispensing, poor sensory properties, and poor antiperspirancy and/or deodorancy performance. Avoidance of premature interaction involves keeping the polymer physically separate from the AP salt. This may be achieved by co-application of the components from independent compositions; such co-application being done concurrently or consecutively, with either the AP salt or the polymer being applied first.

Alternatively, a composition comprising a non-interacting mixture of the AP salt and the polymer may be employed. Such compositions comprise the polymer physically separate from the AP salt. Non-interacting mixtures of this kind are ones where intimate contact between the AP salt and the polymer is not possible. Mixtures of this kind include co-dispersions of the AP salt and the polymer in a non-solvent carrier material. Examples of mixtures that do not meet this criterion include a true solution comprising both AP salt and the polymer and mixtures comprising AP salt encapsulated by the polymer.

In a particular aspect of the present invention, compositions comprising a non-interacting mixture of the AP salt and the polymer are essentially non-aqueous compositions. Essentially non-aqueous compositions comprise less than 10% by weight of water, preferably less than 5% by weight of water, and most preferably less than 1% by weight of water, excluding any water of hydration associated with the AP salt. In addition to being essentially non-aqueous, many compositions comprising both the AP salt and the polymer comprise less than 20% or even less than 10% by weight of polar organic solvents, for example $C_2$ to $C_4$ alcohols (monohydric or polyhydric), like ethanol.

Polymers

The polymers of the present invention are water soluble and comprise Brønsted acid groups. In addition, the polymers act as co-gellants for the AP salt when mixed therewith in the presence of water, for example water in human sweat, at a temperature of 37° C. or less. The co-gelation results in a thickened state of matter—that is to say, the three component system (polymer, AP salt, water) has a higher viscosity than that of an aqueous solution of either the polymer or AP salt alone. Without wishing to be bound by theory, it is believed that the co-gelation involves chemical interaction between electronegative groups on the polymer and polyvalent hydrated metal cations deriving from the antiperspirant salt.

A simple test that may be used to determine whether or not a polymer is able to act as a co-gellant in given as Example 1. The test consists essentially of mixing aqueous solutions of the polymer and the AP salt and looking for an increase in viscosity.

The water solubility of the polymers used in the present invention, when measured at 37° C., is preferably 10 g/l or greater, more preferably 50 g/l or greater, and most preferably 100 g/l or greater. It is required that the polymers form true solutions, rather than dispersions, in water; such true solutions typically having an absorbance of less than 0.2, preferably less than 0.1 (for a 1 cm pathlength at 600 nm) measured using a Pharmacia Biotech Ultrospec 200 Spectrophotometer or similar instrument. It is also desirable that the polymer is water soluble at pH 7; the attainment of said pH generally requiring a certain amount of neutralisation of the Brønsted acid groups present.

The Brønsted acid groups in the polymer may be present in their protonated form or may be present in their neutralised form as salt groups. Both partially-neutralised and fully-neutralised acidic polymers may be employed as co-gellants in the present invention. Suitable Brønsted acid groups include carboxylic acid groups, sulphonic acid groups, and phosphonic acid groups. Carboxylic acid groups are particularly preferred. Brønsted acid groups are preferably present at a concentration of greater than 0.1 mmole per gram of polymer, more preferably at a concentration of greater than 1.0 mmole per gram of polymer, and most preferably at a concentration of greater than 3.0 mmole per gram of polymer. These preferred levels relate to monobasic Brønsted acid groups and should be reduced pro rata for polybasic Brønsted acid groups. Latent Brønsted acid groups, such as anhydrides or other groups that generate Brønsted acid groups on addition to water, may also be present.

Preferred polymers are organic polymers, in particular, organic polymers possessing only limited positive charge—for example, organic polymers having less than 50 mole %, preferably less than 25 mole %, of positively-charged monomer units. Especially preferred organic polymers are non-ionic and anionic polymers. Typical polymers possess carbon backbones, optionally interrupted by ester or amide links.

The acid value of a polymer is a widely used means of characterisation. Acid values generally express the acidity of a polymer in terms of the number of milligrams of potassium hydroxide base required to fully neutralise one gram of the polymer. Thus, the unit of measurement can be abbreviated to mg KOH/g.

Many of the polymers of the present invention have acid values greater than 160. Preferred polymers have acid values greater than 320 or even greater than 450. Particularly preferred polymers have acid values greater than 580. These acid values are based on the polymer in its fully protonated state; that is to say, the actual in-use extent of neutralisation of the polymer is ignored in respect of the 'acid value'. Acid values may be measured experimentally or may be estimated theoretically. When using the latter method, acid anhydride groups present in a polymer should be counted as two acid groups, such anhydrides generally being hydrolysed to di-acids by potassium hydroxide.

The preferred carboxylic acid groups may be introduced into the polymer by inclusion of monomers such as acrylic acid, methacrylic acid, maleic acid, itaconic acid, crotonic acid, maleic anhydride, or itaconyl anhydride in the polymer. When the only source of Brønsted acid groups are anhydride monomers, it is required that the anhydride groups are at least partially hydrolysed prior to use of the polymer. Polymers comprising a mixture of any of the above acid and/or anhydride monomers may also be advantageously employed. Particularly preferred polymers are those derived, at least in part, from maleic acid and/or maleic anhydride monomers.

It is sometimes desirable to include other monomers in the polymer. Suitable monomers include methyl vinyl ether, $C_1$–$C_8$ alkyl acrylates and methacrylates, vinyl acetate, ethylene, and propylene. The inclusion of such monomers may aid polymer synthesis, ease handling and/or formulation of the polymer, and may improve the performance of the polymer as a co-gellant.

The molecular weight of the polymer is preferably in the range of 500 to 5,000,000, in particular 10,000 to 3,000,000 and especially 100,000 to 2,500,000. Selection of an appropriate molecular weight for the polymer may lead to benefits in terms of ease of formulation, product aesthetics (particularly product feel), and product performance.

The polymer is preferably incorporated into a composition in an amount of from 0.5% to 20% by weight, more preferably from 1% to 15% by weight, and most preferably from 2% to 12% by weight of said composition, excluding any volatile propellant present.

In certain aspects of the present invention, the polymer is used in particulate form. When used in such form, the polymer particles generally have sizes between 0.1 and 200 μm, preferably with a mean particle size of from 3 to 50 μm. When the antiperspirant is also used in particulate form, it is further preferred that the polymer be of similar particle size to the AP (vide infra).

The mean particle sizes referred to in this specification are volume means, as typically determined by light scattering techniques.

Antiperspirant Salts

Antiperspirant salts for use herein are often selected from astringent salts including, in particular, aluminium and mixed aluminium/zirconium salts, including both inorganic salts, salts with organic anions, and complexes. Preferred astringent salts are aluminium and aluminium/zirconium halides and halohydrate salts, such as chlorohydrates.

Aluminium halohydrates are usually defined by the general formula $Al_2(OH)_xQ_y \cdot wH_2O$ in which Q represents chlorine, bromine or iodine, x is variable from 2 to 5 and x+y−6 while $wH_2O$ represents a variable amount of hydration. Especially effective aluminium halohydrate salts, known as activated aluminium chlorohydrates, are described in EP006,739 (Unilever PLC and NV). Some activated salts do not retain their enhanced activity in the presence of water but are useful in substantially anhydrous formulations, i.e. formulations that do not contain a distinct aqueous phase.

Zirconium salts are usually defined by the general formula $ZrO(OH)_{2-x}Q_x \cdot wH_2O$ in which Q represents chlorine, bromine or iodine; x is from about 1 to 2; w is from about 1 to 7; and x and w may both have non-integer values. Preferred are zirconyl oxyhalides, zirconiun hyroxyhalides, and combinations thereof. Nonlimiting examples of zirconium salts and processes for making them are described in Belgian Patent 825,146, Schmitz, issued Aug. 4, 1975 and U.S. Pat. No. 4,223,010 (Rubino).

The above aluminium and aluminium/zirconium salts may have coordinated and/or bound water in various quantities and/or may be present as polymeric species, mixtures or complexes.

Suitable aluminium-zirconium complexes often comprise a compound with a carboxylate group, for example an amino acid. Examples of suitable amino acids include tryptophan, β-phenylalanine, valine, methionine, β-alanine and, most preferably, glycine.

It is highly desirable to employ complexes of a combination of aluminium halohydrates and zirconium chlorohydrates together with amino acids such as glycine, which are disclosed in U.S. Pat. No. 3,792,068 (Procter and Gamble Co.). Certain of those Al/Zr complexes are commonly called ZAG in the literature. ZAG actives generally contain aluminium, zirconium and chloride with an Al/Zr ratio in a range from 2 to 10, especially 2 to 6, an Al/Cl ratio from 2.1 to 0.9 and a variable amount of glycine. Actives of this preferred type are available from Westwood, from Summit and from Reheis.

Other actives that may be utilised include astringent titanium salts, for example those described in GB 2,299,506.

Antiperspirant salts are preferably incorporated into a composition in an amount of from 0.5–60%, particularly from 5 to 30% or 40% and especially from 5 or 10% to 30 or 35% of the weight of the composition.

The proportion of solid AP salt in a composition normally includes the weight of any water of hydration and any complexing agent that may also be present in the solid active. However, when the active salt is in solution, its weight excludes any water present.

The weight ratio of the AP salt to the polymer is preferably 25:1 or less, 1:10 or greater, particularly between 25:1 and 1:10, and especially between 10:1 and 1:5.

Frequently the AP salt may be present in a composition taking the form of a suspension in which the AP salt in particulate form is suspended in a water-immiscible liquid carrier. In such compositions, the particle size of the AP salts often falls within the range of 0.1 to 200 μm with a mean particle size often from 3 to 20 μm. Both larger and smaller mean particle sizes can also be contemplated such as from 20 to 50 μm or 0.1 to 31 μm.

Optional Additional Components

A carrier material for the antiperspirant salt and/or the polymer is a highly desirable additional component of the products of the invention. Compositions preferably comprise carrier material at a level of from 30% to 98%, or more preferably from 60% to 97% of the weight of the composition, excluding any volatile propellant present.

The carrier material may be hydrophobic or hydrophilic, solid or liquid. Preferred carrier materials are hydrophobic. It is highly preferred that the solid or liquid carrier material is fluid at the temperatures typically used to make the product form in question. Hydrophobic liquid carrier materials particularly suitable for use are liquid silicones, that is to say, liquid polyorganosiloxanes. Such materials may be cyclic or linear, examples include Dow Corning silicone fluids 344, 345, 244, 245, 246, 556, and the 200 series; Union Carbide Corporation Silicones 7207 and 7158; and General Electric silicone SF1202. Alternatively, non-silicone hydrophobic liquids may be used. Such materials include mineral oils, hydrogenated polyisobutene, polydecene, paraffins, isoparaffins of at least 10 carbon atoms, and aliphatic or aromatic ester oils (e.g. isopropyl myristate, lauryl myristate, isopropyl palmitate, diisopropyl sebecate, diisopropyl adipate, or $C_8$ to $C_{18}$ alkyl benzoates).

Hydrophilic liquid carrier materials that may be used include water and polar organic solvents. When water is used as a carrier material for the polymer and/or the antiperspirant salt, it is strongly preferred that the polymer and the antiperspirant salt are applied from independent compositions. This ensures that premature interaction does not occur between the components (vide supra). Polar organic solvents that may be employed include $C_1$–$C_4$ monohydric alcohols, for example ethanol and isopropanol, and polyols, for example propylene glycol, dipropylene glycol, glycerol, polyethylene glycol, and $C_2$–$C_8$ 1,2-alkanediols like 1,2-hexanediol.

An additional component that can sometimes augment deodorancy performance is an organic anti-microbial agent. Most of the classes of agents commonly used in the art can be incorporated into products of the invention. Levels of incorporation are preferably from 0.01% to 3%, more preferably from 0.03% to 0.5%. Preferred organic anti-microbial agents are those that are more efficacious than simple alcohols such as ethanol. The preferred organic anti-microbials are also bactericides, for example quaternary ammonium compounds, like cetyltrimethylammonium salts; chlorhexidine and salts thereof; and diglycerol monocaprate, diglycerol monolaurate, glycerol monolaurate, and similar materials, as described in "Deodorant Ingredients", S. A. Makin and M. R. Lowry, in "Antiperspirants and Deodorants", Ed. K. Laden (1999, Marcel Dekker, New York). More preferred anti-microbials are polyhexamethylene biguanide salts (also known as polyaminopropyl biguanide salts), an example being Cosmocil CQ available from Zeneca PLC, preferably used at up to 1% and more preferably at 0.03% to 0.3% by weight; 2',4,4'-trichloro,2-hydroxy-diphenyl ether (triclosan), preferably used at up to 1% by weight of the composition and more preferably at 0.05–0.3%; and 3,7,11-trimethyldodeca-2,6,10-trienol (farnesol), preferably used at up to 1% by weight of the composition and more preferably at up to 0.5%.

Structurants and emulsifiers are further additional components that are highly desirable in certain product forms. Structurants, when employed, are preferably present at from 1% to 30% by weight of a composition, whilst emulsifiers are preferably present at from 0.1% to 10% by weight of a composition. In roll-on compositions, such materials help control the rate at which product is dispensed by the roll ball. In stick compositions, such materials can form gels or solids from solutions or suspensions. Suitable structurants for use in such compositions include cellulosic thickeners such as hydroxypropyl cellulose and hydroxyethyl cellulose, fibre-forming structurants such as 12-hydroxystearic acid, esters of 12-hydroxystearic acid, amides of 12-hydroxystearic acid, stearic acid, behenic acid and di- and tri-glycerides thereof, N-lauroyl-glutamic acid dibutyl amide, 2-dodecyl-N,N'-dibutyl-succinamide, and dibenzylidene sorbitol. Partially or fully esterified disaccaharides, for example cellobiose octanoates, may also be used, as may structurants like dextrin palmitate. Sterols (e.g. β-sitoserol) and sterol esters (e.g. oryzanol) are also suitable for use, when used in combination. Emulsion pump sprays, roll-ons, creams, and gel compositions can be formed using a range of oils, waxes, and emulsifiers. Suitable emulsifiers include steareth-2, steareth-20, steareth-21, ceteareth-20, glyceryl stearate, cetyl alcohol, cetearyl alcohol, PEG-20 stearate, and dimethicone copolyol. Suspension aerosols, roll-ons, sticks, and creams require structurants to slow sedimentation (in fluid compositions) and to give the desired product consistency to non-fluid compositions. Suitable structurants include sodium stearate, stearyl alcohol, cetyl alcohol, hydrogenated castor oil, beeswax, synthetic waxes, microcrystalline wax, paraffin waxes, candelilla wax, dibutyl lauroyl glutamide, alkyl silicone waxes, quaternium-18 bentonite, quaternium-18 hectorite, silica, and propylene carbonate. Some of the above materials also function as suspending agents in certain compositions.

Further emulsifiers desirable in certain compositions of the invention are perfume solubilisers and wash-off agents. Examples of the former include PEG-hydrogenated castor oil, available from BASF in the Cremaphor RH and CO ranges, preferably present at up to 1.5% by weight, more preferably 0.3 to 0.7% by weight. Examples of the latter include poly(oxyethylene) ethers.

Certain sensory modifiers are further desirable components in the compositions of the invention. Such materials are preferably used at a level of up to 20% by weight of the composition. Emollients, humectants, volatile oils, non-volatile oils, and particulate solids that impart lubricity are all suitable classes of sensory modifiers. Examples of such materials include cyclomethicone, dimethicone, dimethiconol, isopropyl myristate, isopropyl palmitate, talc, finely-divided silica (e.g. Aerosil 200), particulate polyethylene (e.g. Acumist B18), polysaccharides, corn starch, C12–C15 alcohol benzoate, PPG-3 myristyl ether, octyl dodecanol, C7–C14 isoparaffins, di-isopropyl adipate, isosorbide laurate, PPG-14 butyl ether, glycerol, hydrogenated polyisobutene, polydecene, titanium dioxide, phenyl trimethicone, dioctyl adipate, and hexamethyl disiloxane.

Fragrance is also a desirable additional component in the compositions of the invention. Suitable materials include conventional perfumes, such as perfume oils and also include so-called deo-perfumes, as described in EP 545,556 and other publications. Levels of incorporation are preferably up to 4% by weight, particularly from 0.1% to 2% by weight, and especially from 0.7% to 1.7% by weight.

It should be noted that certain components of compositions perform more than one function. Such components are particularly preferred additional ingredients, their use often saving both money and formulation space. Examples of such components include the many components that can act as both structurants and sensory modifiers, for example silica.

Further additional components that may also be included are colourants and preservatives at a conventional level, for example $C_1$–$C_3$ alkyl parabens.

Product Forms

The products of the invention may comprise compositions taking any form. When the product comprises more than one composition, it is preferred that the compositions take the same form. Example compositions include wax-based sticks, soap-based sticks, compressed powder sticks, roll-on suspensions or solutions, emulsions, gels, creams, squeeze sprays, pump sprays, and aerosols. Each product form contains its own selection of additional components, some essential and some optional. The types of components typical for each of the above product forms may be incorporated in the corresponding compositions of the invention.

Roll-on compositions of the invention preferably have a low level of non-volatile emollient present, for example isopropyl myristate or propylene glycol at 0.2–2% by weight. Antiperspirant sticks have cyclomethicone as a preferred carrier fluid. Also preferably present are one or more ethers or esters previously mentioned as sensory modifiers; these materials can serve to mask deposits. Wash-off agents are also desirable in such compositions.

Aerosol Compositions

Aerosol compositions of the invention are a particularly preferred product form. Preferably the propellant is the major component in such compositions, comprising from 30 to 99 parts by weight, more preferably from 50 to 95 parts by weight.

The propellant is normally selected from liquified hydrocarbons or halogenated hydrocarbon gases (particularly fluorinated hydrocarbons such as 1,1-difluoroethane and/or 1-trifluoro-2-fluoroethane) that have a boiling point of below 10° C. and especially those with a boiling point below 0° C. It is especially preferred to employ liquified hydrocarbon gases, and especially $C_3$ to $C_6$ hydrocarbons, including propane, isopropane, butane, isobutane, pentane and isopentane and mixtures of two or more thereof. Preferred propellants are isobutane, isobutane/isopropane, isobutane/propane and mixtures of isopropane, isobutane and butane.

Other propellants that can be contemplated include alkyl ethers, such as dimethyl ether or compressed non-reactive gasses such air, nitrogen or carbon dioxide.

The base composition, which is mixed with the propellant, may comprise any of the following components as preferred additional ingredients: a carrier material (fluid), a fragrance, an emollient (e.g. isopropyl myristate or propylene glycol) or an anticlogging agent (in order to prevent or minimise the occurrence of solid occlusions in the spray nozzle). Further components may be added to mask powdery deposits, for example non-volatile oils, long chain alcohols (e.g. octyl dodecanol), ethers (e.g. PPG-14 butyl ether), or dimethicone fluids.

An aerosol composition is usually filled into an aerosol canister that is capable of withstanding pressures generated by the formulation, employing conventional filling apparatus and conditions. The canister can conveniently be a commercially available metal canister fitted with a dip tube, valve and spray nozzle through which the formulation is dispensed.

Methods of Manufacture

The details of the relevant methods of manufacture depend upon the product form concerned. For a product that is a composition comprising a non-interacting mixture of the AP salt and the polymer, the basic method comprises the addition of the AP salt and the polymer to a fluid carrier material, keeping the AP salt and the polymer physically separate. In this context, a fluid carrier material is one capable of flow at the temperature used during the manufacture of the product. It is essential that the mixing is done in such a way as to prevent chemical interaction between the AP salt and the polymer. In a particularly preferred method, an essentially anhydrous carrier fluid is employed. It is further preferred that the AP salt and polymer added to the anhydrous carrier fluid are present in particulate form.

EXAMPLES

Example 1

Co-gellant Test for Polymer

An aqueous solution of the polymer is prepared under conditions sufficient to fully hydrolyse any acid anhydride groups present to a concentration of 1.9% w/w. Said solution is mixed with an aqueous solution of antiperspirant salt (50% w/w) in amounts sufficient to give a molar ratio of Brønsted acid group to antiperspirant metal ion of 1:1. If the viscosity of the resulting solution is greater than that of both of the starting solutions, then the polymer is a co-gellant for the antiperspirant.

In a particular example, 0.42 g of a 50% w/w solution of aluminium chlorohydrate was mixed with 9.97 g of a 1.9% solution of Gantrez S-95 (see note to Table 1) to give a molarity of 0.2M for both the aluminium ions and the Brо/nsted acid groups present. A gelled state of matter resulted from the mixing of the two free-flowing solutions.

Examples 2 to 6

Antiperspirancy Test

The following protocol was used to measure the sweat weight reduction (that is to say, the antiperspirancy benefit) resulting from use of the compositions given in Table 1.

The performance of each antiperspirant test product was compared to that of a non-antiperspirant control product on a panel typically consisting of 30 or more women. Before the test, the panellists were required to complete a "wash-out period" of approximately three weeks (17 days minimum). During the wash-out period, the panellists were forbidden from using any deodorant or antiperspirant product, other than a non-antiperspirant deodorant product given to them by the test operators.

After the wash-out period, the test operators applied the antiperspirant test product (0.30 g) to one axilla and the non-antiperspirant control product (0.30 g) to the other axilla of each panellist. This was done once each day for three days. After the third application, panellists were requested not to wash under their arms for the following 24 hours.

24 hours after the third and final product application, the panellists were induced to sweat in a hot-room at 40° C. ($\pm 2°$ C.) and 40% ($\pm 5\%$) relative humidity, for 40 minutes. After this period, the panellists left the hot-room and their axillae were carefully wiped dry. Pre-weighed cotton pads were then applied to each axilla of each panellist and the panellists re-entered the hot-room for a further 20 minutes. Following this period, the pads were removed and re-weighed, enabling the weight of sweat generated to be calculated.

The sweat weight reduction (SWR) for each panellist was calculated as a percentage (% SWR) and the mean % SWR and 95% confidence limits were calculated according to the method described by Murphy and Levine in "Analysis of Antiperspirant Efficacy Results", *J. Soc. Cosmetic Chemists,* 1991 (May), 42, 167–197.

Table 1 gives the mean % SWR and 95% confidence limits resulting from treatment with the indicated compositions.

TABLE 1

The compositional details given in the Tables are weight percentages and that letters designate comparative examples.

| Example: | 2 | A | 3 | 4 | 5 | 6 | B | C |
|---|---|---|---|---|---|---|---|---|
| ACH[1] | 11 | 11 | 0 | 0 | 0 | 0 | 0 | 0 |
| AACH[2] | 0 | 0 | 11 | 11 | 11 | 11 | 11 | 0 |
| Gantrez AN-119[3] | 11 | 0 | 11 | 5.5 | 0 | 0 | 0 | 22 |
| Gantrez S-95[4] | 0 | 0 | 0 | 0 | 11 | 0 | 0 | 0 |
| PAA[5] | 0 | 0 | 0 | 0 | 0 | 5.5 | 0 | 0 |
| Bentone 38V[6] | 3 | 3 | 3 | 3 | 3 | 3 | 3 | 3 |
| Ethanol | 1 | 1 | 1 | 1 | 1 | 0 | 1 | 1 |
| Propylene carbonate | 1 | 1 | 1 | 1 | 1 | 1 | 1 | 1 |
| DC 245[7] | 73 | 84 | 73 | 78.5 | 73 | 79.5 | 84 | 73 |
| % SWR: | 48 | 34 | 51 | 51 | 50 | 49 | 35 | 0 |
| 95% limits | 38–56 | 20–45 | 40–60 | 43–58 | 40–58 | 42–55 | 22–46 | −13–11 |

[1]Aluminium chlorohydrate, Microdry Super Ultra Fine, ex Reheis.
[2]Activated aluminium chlorohydrate, type A296, ex Guilini.
[3]Partially hydrolysed co-polymer of maleic anhydride and methyl vinyl ether (monobasic Brønsted acid group concentration: 3.4 mmole/g; acid value: 695; MW: ca. 216,000), ex International Speciality Products Inc. (ISP)
[4]Co-polymer of maleic acid and methyl vinyl ether (acid value: 592; MW: ca. 216,000), ex ISP.
[5]Poly(acrylic acid), molecular weight about 450,000, ex Polysciences, Inc.
[6]Quaternium-18 hectorite, ex Rheox.
[7]D5 cyclomethicone fluid, ex Dow Corning.

The above roll-on antiperspirant compositions were prepared in the following manner. To a mixture of the propylene carbonate, DC 245, and ethanol when present, was slowly added Bentone 38V, with stirring until homogeneous. The antiperspirant salt and the polymer were then slowly added and stirring was continued until a smooth, homogeneous suspension was formed.

The results in Table 1 illustrate the enhanced antiperspirancy performance of an ACH roll-on composition comprising partially hydrolysed Gantrez AN 119 (Example 2 vs. Example A) and the enhanced antiperspirancy performance of AACH roll-on compositions comprising partially hydrolysed Gantrez AN 119 (Examples 3 and 4), Gantrez S-95 (Example 5), or poly(acrylic acid) (Example 5) in comparison with compositions containing no co-gellant polymer (Example B) or no antiperspirant salt (Example C).

Example 7

Further Antiperspirancy Test

A modification of the protocol described above was used to measure the sweat weight reduction resulting from use of the compositions given in Table 2. The modified protocol differed in using male panellists instead of female; self-application of the test/control products; and hot-room entry 8 to 10 hours after the third and final product application. The compositions were prepared in a similar manner to those of Table 1.

TABLE 2

| Example: | 7 | D | E |
|---|---|---|---|
| AACH[1] | 11 | 11 | 22 |
| Gantrez AN-139[2] | 5.5 | 0 | 0 |
| Bentone 38V | 3 | 3 | 3 |
| Ethanol | 1 | 1 | 1 |
| Propylene carbonate | 1 | 1 | 1 |
| DC 245 | 78.5 | 84 | 73 |
| % SWR: | 56 | 35 | 55 |
| 95% limits | 44–66 | 22–44 | 44–64 |

[1]As previously described (Table 1).
[2]Partially hydrolysed co-polymer of maleic anhydride and methyl vinyl ether (acid value: 696; MW: ca. 1,080,000), ex ISP.

These results illustrate the enhanced antiperspirancy performance of a roll-on composition comprising Gantrez AN-139 (partially hydrolysed), when compared with comparative Example D. Comparison with comparative Example E illustrates that the same antiperspirancy performance can be achieved using less antiperspirant salt, when compositions according to the invention are employed.

Further Roll-on Compositions

The compositions of Table 3 were prepared in a similar manner to those of Tables 1 and 2. All gave a satisfactory antiperspirancy benefit.

TABLE 3

Components as previously described.

| Example: | 8 | 9 | 10 | 11 | 12 | 13 |
|---|---|---|---|---|---|---|
| AACH | 5.5 | 3.2 | 2.2 | 16.5 | 18.8 | 19.8 |
| Gantrez AN-119 | 16.5 | 18.8 | 19.8 | 5.5 | 3.2 | 2.2 |
| Bentone 38V | 3 | 3 | 3 | 3 | 3 | 3 |
| Ethanol | 1 | 1 | 1 | 1 | 1 | 1 |

TABLE 3-continued

Components as previously described.

| Example: | 8 | 9 | 10 | 11 | 12 | 13 |
|---|---|---|---|---|---|---|
| Propylene carbonate | 1 | 1 | 1 | 1 | 1 | 1 |
| DC 245 | 73 | 73 | 73 | 73 | 83 | 73 |

Further Roll-on Compositions

The compositions of Table 4 were prepared in a similar manner to those of Tables 1, 2 and 3. All gave a satisfactory antiperspirancy benefit.

TABLE 4

| Example: | 14 | 15 | 16 | 17 | 18 |
|---|---|---|---|---|---|
| AACH[1] | 0 | 11 | 0 | 0 | 11 |
| AZAG[2] | 11 | 0 | 11 | 11 | 0 |
| Gantrez AN-119[3] | 11 | 0 | 0 | 0 | 0 |
| Gantrez AN-139[4] | 0 | 0 | 5.5 | 0 | 0 |
| Gantrez AN-169[5] | 0 | 5.5 | 0 | 5.5 | 0 |
| Poly(itaconic acid)[6] | 0 | 0 | 0 | 0 | 5.5 |
| Bentone 38V | 3 | 3 | 3 | 3 | 3 |
| Ethanol | 1 | 1 | 1 | 1 | 0 |
| Propylene carbonate | 1 | 1 | 1 | 1 | 1 |
| DC 245 | 73 | 78.5 | 78.5 | 78.5 | 79.5 |

[1]As previously described.
[2]Aluminium zirconium tetrachlorohydrex gly., Q5-7167, ex Summit.
[3]As previously described.
[4]As previously described.
[5]Partially hydrolysed co-polymer of maleic anhydride and methyl vinyl ether (acid value: 695; MW: ca. 1,980,000), ex ISP.
[6]Ex Polysciences, Inc.

Soft Solid Compositions

The soft solid antiperspirant compositions of Table 5 were prepared in the following manner. The Finsolv-TN was heated to about 115° C. and the GP-1 was added, with stirring until the GP-1 had dissolved. The mixture was then cooled to about 90° C. and the dextrin palmitate was added, again with stirring until dissolved. The mixture was then cooled to about 75–80° C. and the AACH and AN-119 were added. Stirring was re-commenced until a homogeneous mixture was obtained. The mixture was then cooled to about 70° C. and transferred to an appropriate dispenser.

After cooling to ambient temperature, both products were assessed as previously described and were found to give a satisfactory antiperspirancy benefit.

TABLE 5

| Example: | 19 | 20 |
|---|---|---|
| AACH[1] | 12.75 | 25.5 |
| Gantrez AN-119[2] | 12.75 | 12.75 |
| GP-1[3] | 1 | 1 |
| Dextrin palmitate | 5 | 5 |
| Finsolv-TN[4] | 68.5 | 55.75 |

[1]Activated aluminium chlorohydrate, A-418, ex Summit.
[2]As previously described.
[3]N-lauroyl-L-glutamic acid di-n-butylamide, ex Ajinomoto.
[4]C12–15 alkyl benzoate, ex Finetex.

Aerosol Compositions

The aerosol antiperspirant compositions of Table 6 were prepared and packaged in the following manner. The DC245 and the Bentone 38V were stirred together until a homogeneous mixture was obtained. The fragrance material was then added with stirring. Stirring was then stopped whilst the AACH and AN-119 were added. Stirring was re-commenced and continued until a homogeneous mixture was obtained. The resulting mixture was transferred into a conventional aluminium deodorant can, having valve access, and the CAP 40 liquefied volatile propellant was introduced into the can from a propellant 'transfer can', via the valve, using a polyethylene transfer device. Finally, the can was fitted with a suitable actuator to enable effective spray application of the product.

TABLE 6

| Example | 21 | 22 | 23 |
|---|---|---|---|
| AACH[1] | 8 | 9 | 4 |
| Gantrez AN-119[2] | 2 | 1 | 1 |
| Fragrance | 0.65 | 0.65 | 0.3 |
| DC245 | 14.25 | 14.25 | 7.1 |
| CAP 40[3] | 75.1 | 75.1 | 87.6 |

[1]Activated aluminium chlorohydrate, type A296, ex Guilini.
[2]As previously described.
[3]Propellant, proprietary mix of butane, isobutane and propane, ex Calor.

All the products were assessed as previously described and were found to give a satisfactory antiperspirancy benefit.

Stick Compositions

The stick compositions of Table 7 were prepared in the following manner. The stearyl alcohol, PEG distearate, Castorwax MP80, and DC245 were heated to about 90° C., with stirring until a homogeneous mixture was obtained. The talc was then added, and mixed in, followed by the AZAG and the AN-119. Stirring was re-commenced and continued for a further 5 minutes to give a homogeneous mixture. Finally, the fragrance material was added and mixed in and the composition was transferred to a suitable dispenser to cool and solidify.

TABLE 7

| Example | 24 | 25 | 26 |
|---|---|---|---|
| AZAG[1] | 24 | 12 | 24 |
| AN-119[2] | 12 | 12 | 6 |
| Fragrance | 1 | 1 | 1 |
| Castorwax MP80[3] | 4 | 4 | 4 |
| Stearyl alcohol[4] | 14 | 14 | 14 |
| PEG distearate[5] | 1 | 1 | 1 |
| Talc[6] | 3.2 | 3.2 | 3.2 |
| DC245 | to 100 | to 100 | to 100 |

[1]Aluminium zirconium tetrachlorohydrex gly., Q5-7167, ex Summit.
[2]As previously described.
[3]Hydrogenated castor wax, ex Aston Chemicals.
[4]Lanette 18, ex Henkel.
[5]Estol EO4 DS 3724, ex Unichema.
[6]Superfino talc, ex Cyprus Minerals.

What is claimed is:

1. An antiperspirant product comprising an antiperspirant salt and a water soluble polymer, wherein:
   (i) the polymer comprises Brønsted acid groups and acts as a co-gellant for the antiperspirant salt when mixed therewith in the presence of water; and
   (ii) the polymer is physically separate from antiperspirant salt prior to application.

2. An antiperspirant product according to claim 1, wherein the polymer is an organic polymer having less than 50 mole % of positively-charged monomer units.

3. An antiperspirant product according to claim 1, wherein the polymer is an organic polymer possessing a carbon backbone, optionally interrupted by ester or amide groups.

4. An antiperspirant product according to claim 2, wherein the polymer is nonionic or anionic.

5. An antiperspirant product according to claim 1, wherein the polymer has an acid value of greater than 160.

6. An antiperspirant product according to claim 1, wherein the polymer comprises carboxylic acid groups.

7. An antiperspirant product according to claim 6, wherein the polymer is derived, at least in part, from maleic acid or maleic anhydride monomer units.

8. An antiperspirant product according to claim 1, comprising a composition comprising a carrier material.

9. An antiperspirant product according to claim 8, wherein the carrier material is a hydrophobic liquid.

10. An antiperspirant product according to claim 1, comprising an aerosol composition comprising a volatile propellant.

11. An antiperspirant product according to claim 1, comprising a stick composition comprising a structurant.

12. An antiperspirant product according to claim 1, comprising a cream composition comprising a structurant and/or an emulsifier.

13. An antiperspirant product according to claim 1, comprising an organic antimicrobial agent.

14. An antiperspirant product according to claim 1, having the antiperspirant salt and the polymer present in independent compositions.

15. An antiperspirant product according to claim 1, that is a composition comprising a non-interacting mixture of the antiperspirant salt and the polymer.

16. An antiperspirant product according to claim 15, that is essentially anhydrous.

17. An antiperspirant product according to claim 15, wherein the weight ratio of the antiperspirant salt to the polymer is 25:1 or less.

18. An antiperspirant product according to claim 15, wherein the weight ratio of the antiperspirant salt to the polymer is 1:10 or greater.

19. A cosmetic method of achieving an antiperspirancy and/or deodorancy benefit, said method comprising the topical application to the human body of an antiperspirant product as defined in claim 1.

20. A cosmetic method of achieving an antiperspirancy and/or deodorancy benefit, said method comprising bringing together on the surface of the human body an antiperspirant salt and a water soluble polymer comprising Brønsted acid groups which, in the presence of water, acts as a co-gellant for the antiperspirant salt.

21. A method for the manufacture of an antiperspirant composition according to claim 15, comprising the mixing, in a fluid carrier material, of the antiperspirant salt and the polymer.

* * * * *